US00PP31124P2

(12) United States Plant Patent
Vandenberg

(10) Patent No.: US PP31,124 P2
(45) Date of Patent: Nov. 26, 2019

(54) ***HIBISCUS* PLANT NAMED 'PASSION WIND'**

(50) Latin Name: *Hibiscus rosa-sinensis*
Varietal Denomination: Passion Wind

(71) Applicant: Cornelis P. Vandenberg, Fort Myers, FL (US)

(72) Inventor: Cornelis P. Vandenberg, Fort Myers, FL (US)

(73) Assignee: ARIS HORTICULTURE, INC., Barberton, OH (US)

( * ) Notice: Subject to any disclaimer, the term of this patent is extended or adjusted under 35 U.S.C. 154(b) by 0 days.

(21) Appl. No.: 15/999,917

(22) Filed: Aug. 29, 2018

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ... A01H 5/02; A01H 5/00; A01H 6/60; A01H 6/608
See application file for complete search history.

*Primary Examiner* — June Hwu
(74) *Attorney, Agent, or Firm* — C. A. Whealy

(57) ABSTRACT

A new and distinct cultivar of *Hibiscus* plant named 'Passion Wind', characterized by its semi-upright, uniformly mounded plant habit appropriate for container production; freely branching habit, dense and bushy appearance; glossy dark green-colored leaves; uniform and freely flowering habit; large red purple-colored flowers with dark red-colored centers; and good postproduction and garden performance.

2 Drawing Sheets

Botanical designation: *Hibiscus rosa-sinensis.*
Cultivar denomination: 'PASSION WIND'.

BACKGROUND OF THE INVENTION

The present invention relates to a new and distinct *Hibiscus* plant, botanically known as *Hibiscus rosa-sinensis* and hereinafter referred to by the name 'Passion Wind'.

The new *Hibiscus* plant is a product of a planned breeding program conducted by the Inventor in Alva, Fla. The objective of the breeding program is to create new freely-branching *Hibiscus* plants with a dense, uniform and compact plant habit appropriate for container production, early and uniform flowering habit, numerous flowers per lateral branch, desirable flower color and good garden performance.

The new *Hibiscus* plant originated from a cross-pollination made by the Inventor in Alva, Fla. in 2009 of a proprietary selection of *Hibiscus rosa-sinensis* identified as code number 2017, not patented, as the female, or seed, parent with a proprietary selection of *Hibiscus rosa-sinensis* identified as code number 2691, not patented, as the male, or pollen, parent. The new *Hibiscus* plant was discovered and selected by the Inventor as a single flowering plant within the progeny of the stated cross-pollination in a controlled greenhouse environment in Alva, Fla. on Jul. 16, 2012.

Asexual reproduction of the new *Hibiscus* plant by vegetative terminal cuttings in a controlled greenhouse environment in Alva, Fla. since September, 2012 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Passion Wind'. These characteristics in combination distinguish 'Passion Wind' as a new and distinct *Hibiscus* plant:

1. Semi-upright, uniformly mounded plant habit appropriate for container production.
2. Freely branching habit, dense and bushy appearance.
3. Glossy dark green-colored leaves.
4. Uniform and freely flowering habit.
5. Large red purple-colored flowers with dark red-colored centers.
6. Good postproduction and garden performance.

Plants of the new *Hibiscus* can be compared to plants of the female parent selection. Plants of the new *Hibiscus* differ primarily from plants of the female parent selection in the following characteristics:

1. Plants of the new *Hibiscus* are more uniform in plant habit than plants of the female parent selection.
2. Plants of the new *Hibiscus* are more uniform in flowering habit than plants of the female parent selection.
3. Plants of the new *Hibiscus* and the female parent selection differ in flower color as plants of the female parent selection have darker red purple-colored flowers.

Plants of the new *Hibiscus* can be compared to plants of the male parent selection. Plants of the new *Hibiscus* differ primarily from plants of the male parent selection in the following characteristics:

1. Plants of the new *Hibiscus* are more freely flowering than plants of the male parent selection.

2. Plants of the new *Hibiscus* and the male parent selection differ in flower color as plants of the male parent selection have red-colored flowers.

Plants of the new *Hibiscus* can be compared to plants of the *Hibiscus rosa-sinensis* 'Cayman Wind', disclosed in U.S. Plant Pat. No. 23,760. In side-by-side comparisons plants of the new *Hibiscus* differ from plants of 'Cayman Wind' in the following characteristics:

1. Plants of the new *Hibiscus* are more compact in plant habit than plants of 'Cayman Wind'.
2. Plants of the new *Hibiscus* are more freely branching than plants of 'Cayman Wind'.
3. Plants of the new *Hibiscus* are more uniform in flowering habit than plants of 'Cayman Wind'.
4. Plants of the new *Hibiscus* have slightly smaller flowers than plants of 'Cayman Wind'.
5. Plants of the new *Hibiscus* and 'Cayman Wind' differ in flower color as plants of the new *Hibiscus* have red purple-colored flowers with dark red-colored centers whereas plants of 'Cayman Wind' have intense pink-colored flowers with dark red-colored centers.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of typical flowering plants of 'Passion Wind' grown in a container.

The photograph on the second sheet comprises a close-up view of a typical flowering plant of 'Passion Wind'.

DETAILED BOTANICAL DESCRIPTION

The aforementioned photographs and following observations, measurements and values describe plants grown during the summer in 20-cm containers in a polyethylene-covered greenhouse in Alva, Fla. and in an outdoor nursery in Fort Worth, Tex. under cultural practices which closely approximate commercial *Hibiscus* production. During the production of the plants, day temperatures ranged from 21° C. to 35° C., night temperatures ranged from 12° C. to 21° C. and light levels ranged from 5,000 to 8,000 foot-candles. Plants were pinched three times and were ten months old when the photographs and the description were taken. In the description, color references are made to The Royal Horticultural Society Colour Chart, 2007 Edition, except where general terms of ordinary dictionary significance are used.

Botanical classification: *Hibiscus rosa-sinensis* 'Passion Wind'.

Parentage:

*Female, or seed, parent*.—Proprietary selection of *Hibiscus rosa-sinensis* identified as code number 2017, not patented.

*Male or pollen parent*.—Proprietary selection of *Hibiscus rosa-sinensis* identified as code number 2691, not patented.

Propagation:

*Type*.—By vegetative terminal cuttings.

*Time to initiate and develop roots, summer and winter*.—About four weeks.

*Root description*.—Thick, fibrous; white in color.

*Rooting habit*.—Moderate branching; moderately dense.

Plant description:

*Plant form and growth habit*.—Perennial, evergreen, semi-upright, compact and uniformly mounded plant habit; moderately vigorous to vigorous growth habit.

*Branching habit*.—Freely branching habit with lateral branches potentially develop at every node; pinching enhances lateral branch development; dense and bushy appearance.

*Plant height*.—About 42 cm.

*Plant diameter* (*area of spread*).—About 56 cm.

Lateral branch description:

*Length*.—About 28 cm.

*Diameter*.—About 1 cm.

*Internode length*.—About 1.8 cm.

*Aspect*.—Upright to outwardly spreading.

*Texture and luster, immature*.—Smooth, glabrous; glossy.

*Texture and luster, mature*.—Woody and rough; matte.

*Color, immature*.—Close to 146A.

*Color, mature*.—Close to N199B.

Leaf description:

*Arrangement*.—Alternate, single; numerous; symmetrical.

*Length*.—About 8 cm.

*Width*.—About 7.2 cm.

*Shape*.—Broadly ovate to cordate with truncate tendencies.

*Apex*.—Acute.

*Base*.—Cordate to truncate.

*Margin*.—Crenate.

*Texture and luster, upper surface*.—Smooth, glabrous; glossy.

*Texture and luster, lower surface*.—Smooth, glabrous; somewhat glossy.

*Venation pattern*.—Pinnate; arcuate.

*Color*.—Developing leaves, upper surface: More green than N137A. Developing leaves, lower surface: More green than 146A. Fully expanded leaves, upper surface: Darker green than 147A; venation, close to 147A. Fully expanded leaves, lower surface: More green than 147B; venation, close to 146A.

*Petioles*.—Length: About 5.4 cm. Diameter: About 4 mm. Texture and luster, upper and lower surfaces: Pubescent; slightly glossy. Color, upper and lower surfaces: Close to 146A.

Flower description:

*Flower arrangement and flowering habit*.—Rounded star-shaped single flowers arranged at terminal leaf axils; uniform and freely flowering habit with about three or four flowers per terminal; flowers face mostly upright to slightly outwardly.

*Natural flowering season*.—Plants of the new *Hibiscus* flower naturally during the spring and summer or during periods of warm weather; plants flower year-round in the greenhouse.

*Flower longevity*.—Depending on temperatures and water status, flowers typically last about two to three days on the plant; flowers persistent.

*Flower diameter*.—Large, about 13 cm.

*Flower length* (*height*).—About 8.5 cm.

*Flower buds*.—Resistance to abscission during shipping: Plants of the new *Hibiscus* have been observed to resist flower bud drop during shipping. Length: About 2 cm. Diameter: About 1.3 cm. Shape: Ovoid. Texture and luster: Smooth, glabrous; slightly glossy. Color: More green than 146A.

*Petals*.—Arrangement: Corolla consists of a single whorl of five petals that are fused at base; petals imbricate. Length: About 8.75 cm. Width: About 6.25 cm. Shape: Roughly spatulate. Apex: Rounded. Base: Attenuate. Margin: Entire; slightly undulate. Texture and luster, upper surface: Smooth, glabrous; velvety; slightly glossy. Texture and luster, lower surface: Glabrous, veins prominent; slightly glossy. Color: When opening and fully opened, upper surface: Close to 50A; towards the base, close to 53A; venation, similar to lamina, close to 50A and 53A. When opening and fully opened, lower surface: Close to 50B; towards the base, close to 53B to 53C; where petals overlap, tinted with close to 11B; venation, close to 50B.

*Sepals*.—Appearance: Five sepals in a single whorl fused into a tubular star-shaped calyx. Length: About 2.5 cm. Width: About 1.2 cm. Shape: Lanceolate. Apex: Acuminate. Margin: Entire. Texture and luster, upper surface: Smooth, glabrous; waxy; glossy. Texture and luster, lower surface: Smooth, glabrous; matte. Color, upper surface: Close to 146C. Color, lower surface: More green than 146A.

*Epicalyx*.—Appearance: About six or seven in a single whorl fused at base. Length: About 1.6 cm. Width: About 5 mm. Shape: Lanceolate. Apex: Acuminate. Margin: Entire. Texture and luster, upper and lower surfaces: Smooth, glabrous; matte. Color, upper and lower surfaces: More green than 147A.

*Peduncles*.—Length: About 3 cm. Diameter: About 2.5 mm. Aspect: Mostly upright to slightly outwardly. Strength: Strong, flexible. Texture and luster: Smooth, glabrous; matte. Color: Close to 144A.

*Reproductive organs*.—Androecium: Stamen number: Numerous, about 50 per flower. Filament length: About 1.25 cm. Filament color: Close to 46A. Anther shape: Curved. Anther length: About 1 mm. Anther color: Close to 13A. Amount of pollen: None observed. Gynoecium: Pistil number: One per flower. Pistil length: About 8 cm. Style length: About 6.75 cm. Style texture: Smooth, glabrous; waxy. Style color: Close to 46A. Stigma appearance: Five-parted, rounded. Stigma color: Close to 53A. Ovary color: Close to 11C to 11D.

*Seeds and fruits*.—To date, seed and fruit production has not been observed on plants of the new *Hibiscus*.

Garden performance: Plants of the new *Hibiscus* have been observed to have good garden performance and to tolerate wind, rain and temperatures ranging from about 1° C. to about 37° C.

Pathogen & pest resistance: To date, plants of the new *Hibiscus* grown under Florida production conditions have not been shown to be resistant to pathogens and pests common to *Hibiscus* plants.

It is claimed:

1. A new and distinct *Hibiscus* plant named 'Passion Wind' as illustrated and described.

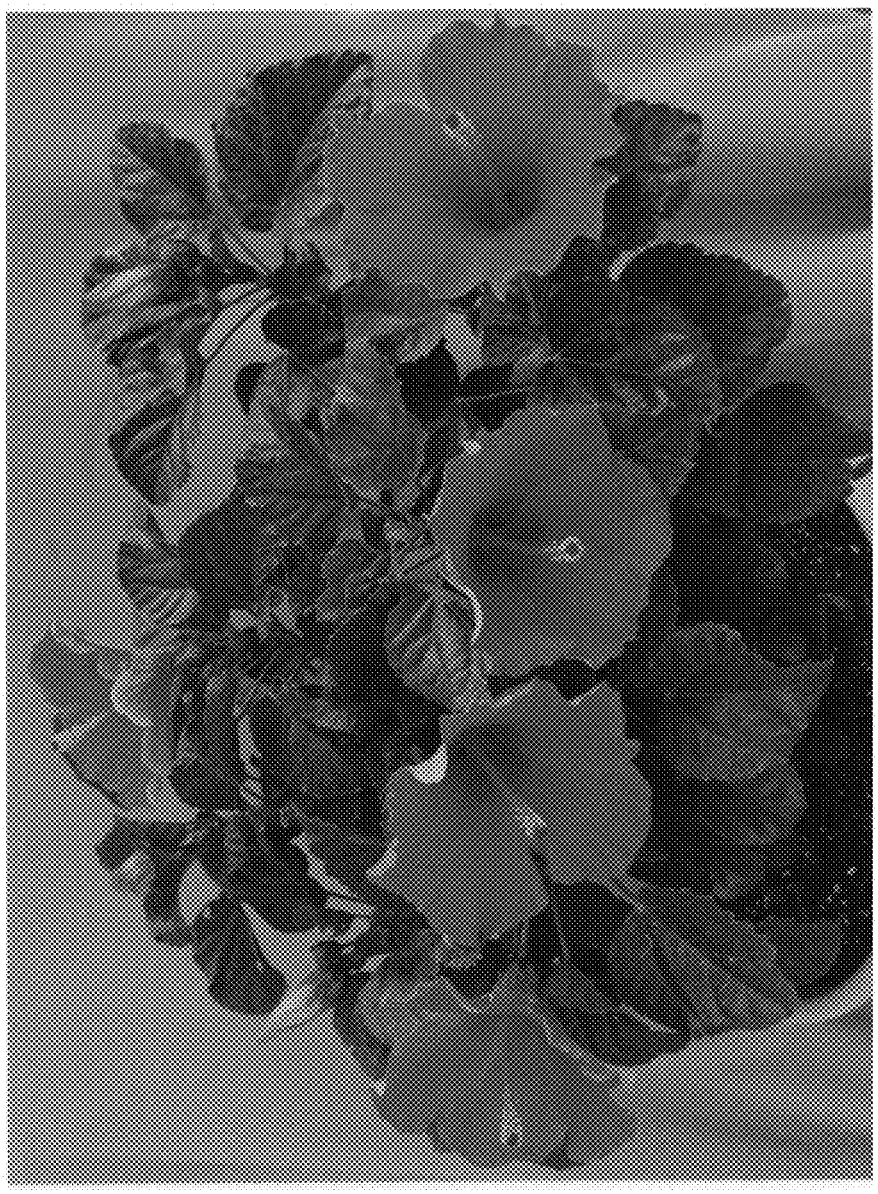

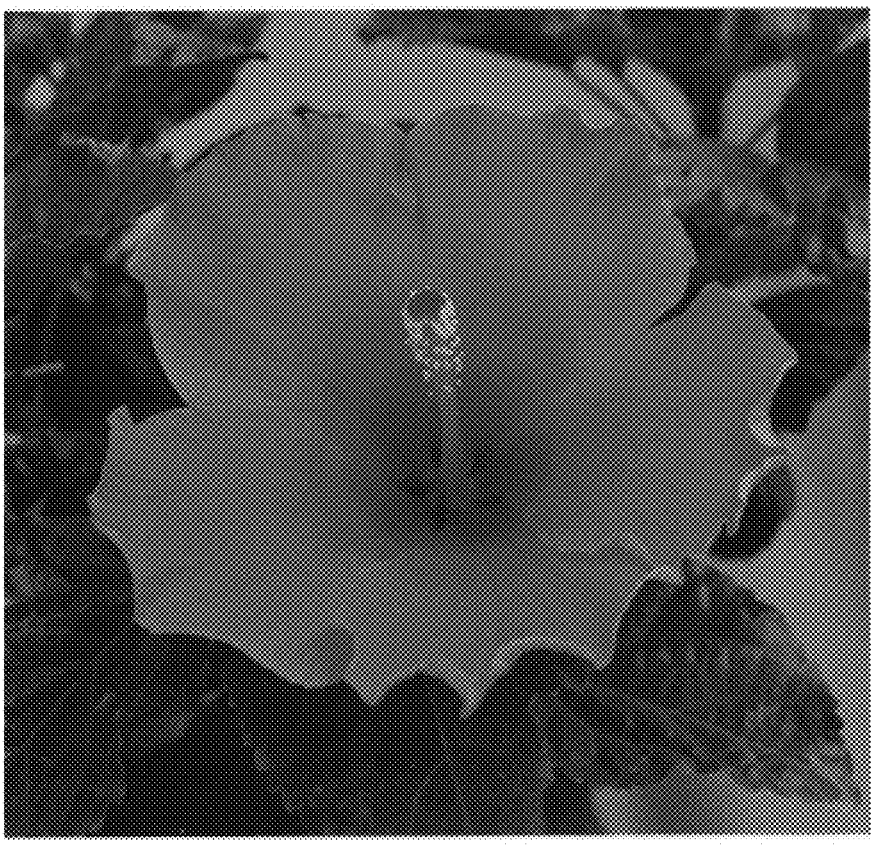

* * * * *